(12) United States Patent
Tanaka et al.

(10) Patent No.: US 6,613,935 B2
(45) Date of Patent: Sep. 2, 2003

(54) PROCESS FOR PRODUCING 1-ACYL-1-CYCLOPROPANECARBOXYLATE DERIVATIVES

(75) Inventors: Hiroki Tanaka, Arai (JP); Li Rui Pan, Arai (JP); Kiyoshi Ikura, Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/241,592

(22) Filed: Sep. 12, 2002

(65) Prior Publication Data

US 2003/0065212 A1 Apr. 3, 2003

(30) Foreign Application Priority Data

Oct. 2, 2001 (JP) ........................ 2001-305917

(51) Int. Cl.$^7$ .............................................. C07C 69/74
(52) U.S. Cl. ...................................... 560/124
(58) Field of Search ......................... 560/124

(56) References Cited

FOREIGN PATENT DOCUMENTS

| EP | 357047 | * | 3/1990 |
| JP | 116183 | * | 4/1994 |
| JP | 11-240867 A | | 9/1999 |

OTHER PUBLICATIONS

Vasil'ev, A.A et al, Izvestiya Akademii Naic SSSR, Seriya Khimicheskaya (1990),(3) 710–12.*

Petrosyan et al., Russian Chemical Bulletin, 43(1): 84–88 (1994).

* cited by examiner

Primary Examiner—Paul J. Killos
(74) Attorney, Agent, or Firm—Birch, Stewart, Kolasch & Birch, LLP

(57) ABSTRACT

A process includes allowing a β-ketoester derivative represented by following Formula (1):

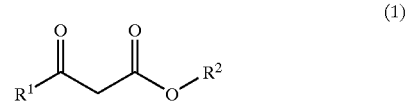

(1)

wherein $R^1$ is a hydrogen atom or a hydrocarbon group; and $R^2$ is a hydrocarbon group, to react with 1,2-dichloroethane and there by produces a 1-acyl-1-cyclopropanecarboxylate derivative represented by following Formula (2):

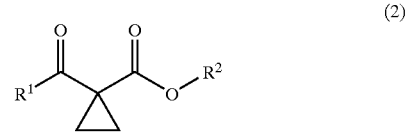

(2)

wherein $R^1$ and $R^2$ have the same meanings as defined above.

1 Claim, No Drawings

PROCESS FOR PRODUCING 1-ACYL-1-CYCLOPROPANECARBOXYLATE DERIVATIVES

BACKGROUND OF THE INVENTION

1. Field of the Invention

The present invention relates to a process for producing 1-acyl-1-cyclopropanecarboxylate derivatives from β-ketoester derivatives. The 1-acyl-1-cyclopropanecarboxylate derivatives are useful as, for example, pharmaceutical intermediates.

2. Description of the Related Art

Conventionally, 1-acyl-1-cyclopropanecarboxylate derivatives have been produced by, for example, a process disclosed in Japanese Unexamined Patent Application Publication No. 11-240867 in which ethyl acetoacetate is allowed to react with 1,2-dibromoethane in the presence of potassium carbonate to thereby yield a 1-acyl-1-cyclopropanecarboxylate. However, 1,2-dibromoethane used in this process is highly toxic, is expensive and cannot significantly be obtained in large quantity.

Alternatively, Russ. Chem. Bl., 43, 1, 84–88, (1994) discloses a process in which a 1-acyl-1-cyclopropanecarboxylate derivative is obtained by electrolysis using 1,2-dichloroethane. However, this process requires special facilities for electrolysis and is low in productivity.

SUMMARY OF THE INVENTION

Accordingly, an object of the present invention is to provide a process for efficiently producing 1-acyl-1-cyclopropanecarboxylate derivatives at low cost. Such 1-acyl-1-cyclopropanecarboxylate derivatives are useful as pharmaceutical intermediates.

After intensive investigations to achieve the above and other objects, the present inventors have found that a corresponding 1-acyl-1-cyclopropanecarboxylate derivative can easily be produced by allowing a β-ketoester derivative such as an acetoacetate derivative to react with 1,2-dichloroethane that is readily available at low cost.

Specifically, the present invention provides a process for producing a 1-acyl-1-cyclopropanecarboxylate derivative. The process includes the step of allowing a β-ketoester derivative represented by following Formula (1):

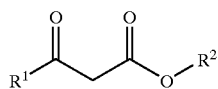

(1)

wherein $R^1$ is a hydrogen atom or a hydrocarbon group; and $R^2$ is a hydrocarbon group, to react with 1,2-dichloroethane to thereby yield a 1-acyl-1-cyclopropanecarboxylate derivative represented by following Formula (2):

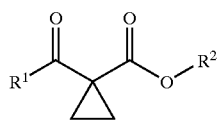

(2)

wherein $R^1$ and $R^2$ have the same meanings as defined above.

According to the present invention, 1-acyl-1-cyclopropanecarboxylate derivatives which are useful as, for example, pharmaceutical intermediates can efficiently be produced at low cost.

DESCRIPTION OF THE PREFERRED EMBODIMENTS

In the β-ketoester derivatives represented by Formula (1), $R^1$ is a hydrogen atom or a hydrocarbon group, and $R^2$ is a hydrocarbon group.

Such hydrocarbon groups in $R^1$ and $R^2$ include aliphatic hydrocarbon groups, alicyclic hydrocarbon groups, aromatic hydrocarbon groups, and hydrocarbon groups each comprising a plurality of these groups combined with each other.

The aliphatic hydrocarbon groups include, but are not limited to, methyl, ethyl, propyl, isopropyl, butyl, isobutyl, s-butyl, t-butyl, pentyl, hexyl, decyl, dodecyl, and other alkyl groups each containing from about 1 to about 10, and preferably from about 1 to about 4 carbon atoms; vinyl, allyl, 1-butenyl, and other alkenyl groups each containing from about 2 to about 10, and preferably from about 2 to about 4 carbon atoms; ethynyl, propynyl, and other alkynyl groups each containing from about 2 to about 10, and preferably from about 2 to about 4 carbon atoms.

The alicyclic hydrocarbon groups include, but are not limited to, cyclopropyl, cyclobutyl, cyclopentyl, cyclohexyl, cyclooctyl, and other cycloalkyl groups each containing from about 3 to about 20, preferably from about 3 to about 15, and more preferably from about 5 to about 8 members; cyclopentenyl, cyclohexenyl, and other cycloalkenyl groups each containing from about 3 to about 20, preferably from about 3 to about 15, and more preferably from about 5 to about 8 members.

The aromatic hydrocarbon groups include, but are not limited to, phenyl, naphthyl, and other aromatic hydrocarbon groups each containing from about 6 to about 14, and preferably from about 6 to about 10 carbon atoms.

Hydrocarbon groups each comprising an aliphatic hydrocarbon group and an alicyclic hydrocarbon group combined with each other include, but are not limited to, cyclopentylmethyl, cyclohexylmethyl, 2-cyclohexylethyl, and other cycloalkyl-alkyl groups such as $C_3$–$C_{20}$ cycloalkyl-$C_1$–$C_4$ alkyl groups.

Hydrocarbon groups each comprising an aliphatic hydrocarbon group and an aromatic hydrocarbon group combined with each other include, but are not limited to, aralkyl groups (e.g., $C_7$–$C_{18}$ aralkyl groups), and alkyl-substituted aryl groups (e.g., phenyl or naphthyl group having from about one to about four $C_1$–$C_4$ alkyl groups substituted thereon).

In the present invention, $R^1$ is preferably a $C_1$–$C_4$ aliphatic hydrocarbon group, of which methyl group is typically preferred. The substituent $R^2$ is preferably a $C_1$–$C_4$ aliphatic hydrocarbon group.

The amount of 1,2-dichloroethane is generally equal to or more than 0.8 mole (e.g., from about 0.8 to about 3 moles) per mole of β-ketoester derivative represented by Formula (1).

A reaction is generally performed in the coexistence of a base. Such bases include inorganic bases and organic bases. Such inorganic bases include, but are not limited to, sodium carbonate, potassium carbonate, and other alkali metal carbonates; sodium hydrogencarbonate, potassium hydrogencarbonate, and other alkali metal hydrogencarbonates; sodium hydroxide, potassium hydroxide, and other alkali metal hydroxides; sodium hydride, potassium hydride, and other alkali metal hydrides; magnesium carbonate, calcium carbonate, and other alkaline earth metal carbonates;

magnesium hydroxide, calcium hydroxide, and other alkaline earth metal hydroxides. Such organic bases include, but are not limited to, triethylamine, and other amines; and pyridine, and other nitrogen-containing heterocyclic compounds. Among these bases, alkali metal carbonates are preferred, of which potassium carbonate is typically preferred. Each of these bases can be used alone or in combination.

The amount of the base is set depending on its type and is generally from about 0.5 to about 4 moles, and preferably from about 0.6 to about 2.5 moles per mole of the β-ketoester derivative represented by Formula (1). For example, when an alkali metal carbonate is used as the base, the amount is generally from about 0.5 to about 2 moles, and preferably from about 0.6 to about 1.5 moles per mole of the β-ketoester derivative. When an alkali metal hydroxide is used as the base, the amount is generally from about 2 to about 4 moles, and preferably from about 2 to about 2.5 moles per mole of the β-ketoester derivative.

The reaction is performed in the presence of, or in the absence of, a solvent. Such solvents are not specifically limited, as long as they do not adversely affect the progress of the reaction. Examples of the solvents include N,N-dimethylformamide, N,N-dimethylacetamide, and other amides; benzonitrile, and other nitriles; diethyl ether, t-butyl methyl ether, dimethoxyethane, diethoxyethane, tetrahydrofuran, and other chain or cyclic ethers. Among them, preference is given to N,N-dimethylformamide, N,N-dimethylacetamide, and other amides; dimethoxyethane, diethoxyethane, and other glycol ethers, and other polar solvents. Each of these solvents can be used alone or in combination. An excess amount of 1,2-dichloroethane (a reacting agent) can be used as a solvent.

When plural types of solvents are used in combination, the ratio of these solvents may significantly affect the reaction time and yield in some cases. More specifically, when 1,2-dichloroethane and a polar solvent such as N,N-dimethylacetamide are used in combination, the reaction time is prolonged if the ratio of 1,2-dichloroethane to the polar solvent is excessively large. In contrast, the reaction time is shortened but the yield is decreased if the ratio of the polar solvent such as N,N-dimethylformamide to 1,2-dichloroethane is excessively large. Accordingly, the weight ratio of 1,2-dichloroethane to the polar solvent such as N, N-dimethylformamide is preferably from about 1:3 to about 5:1 and more preferably from about 1:1 to about 5:3. The total amount of the solvents is, for example, from about 2 to about 30 times by weight, and preferably from about 4 to about 10 times by weight as much as the charged amount of the β-ketoester derivative represented by Formula (1).

To shorten the reaction time and to increase the yield, a reaction system may further comprise an alkali metal halide. Such alkali metal halides include, but are not limited to, alkali metal chlorides such as sodium chloride and potassium chloride; alkali metal bromides such as sodium bromide and potassium bromide; and alkali metal iodides such as sodium iodide and potassium iodide. Each of these alkali metal halides can be used alone or in combination. The amount of the alkali metal halide is, for example, from about 0.01 to about 1.0 mole, and preferably from about 0.03 to about 0.2 mole per mole of the β-ketoester derivative represented by Formula (1).

A reaction temperature can appropriately be selected depending on the type of the β-ketoester derivative represented by Formula (1) and is, for example, from about 60° C. to about 150° C., and preferably from about 80° C. to about 100° C.

The reaction can be performed at ordinary pressure (ambient pressure) or under a pressure (under a load) in a conventional system such as a batch system, semi-batch system or continuous system.

As a result of the reaction, a 1-acyl-1-cyclopropanecarboxylate derivative represented by Formula (2) corresponding to the β-ketoester derivative represented by Formula (1) is produced.

After the completion of the reaction, reaction products can be separated and purified, for example, by a separation means such as filtration, concentration, distillation, extraction, crystallization, recrystallization, adsorption, and column chromatography, or any combination of these separation means.

EXAMPLES

The present invention will be illustrated in further detail with reference to several examples below, which are not intended to limit the scope of the invention.

NMR spectra were determined at 270 MHz ($^1$H-NMR) with tetramethylsilane as an internal standard using a nuclear magnetic resonance spectrometer JNM-EX 270 available from JEOL Ltd. Coupling constants (Hz) are indicated by J.

Example 1

Production of Ethyl 1-Acetyl-1-cyclopropanecarboxylate

A total of 165.6 g of potassium carbonate, 390.0 g of 1,2-dichloroethane, 234.0 g of N,N-dimethylacetamide, 5.0 g of potassium iodide, and 78.0 g of ethyl acetoacetate were mixed, followed by a reaction at 100° C. for 4 hours. The reaction mixture was cooled to room temperature and was filtrated, the resulting filtrate was washed with two portions of 5% by weight hydrochloric acid, and the organic layer was washed with water. The organic layer was then concentrated under a reduced pressure to distill off 1,2-dichloroethane, was subjected to distillation under a reduced pressure and thereby yielded 31.7 g of ethyl 1-acetyl-1-cyclopropanecarboxylate as a colorless liquid as a fraction at 80° C./20 mmHg.

[Spectral data]
$^1$H-NMR (CDCl$_3$) δ: 1.27–1.32 (t, 3H, J=6.75, C$\underline{H}_3$CH$_2$O), 1.47 (s, 4H, CC$\underline{H}_2$C$\underline{H}_2$), 2.47 (s, 3H, C$\underline{H}_3$COC), 4.17–4.25 (q, 2H, CH$_3$C$\underline{H}_2$O)

Example 2

Production of Methyl 1-Acetyl-1-cyclopropanecarboxylate

A total of 662.4 g of potassium carbonate, 1161.2 g of 1,2-dichloroethane, 696.7 g of N,N-dimethylacetamide, 33.2 g of potassium iodide, and 464.5 g of methyl acetoacetate were mixed, followed by a reaction at 100° C. for 13 hours. The reaction mixture was cooled to room temperature and was filtrated, the resulting filtrate was washed with two portions of 5% by weight hydrochloric acid, and the organic layer was washed with water. The washing with the aqueous layer was extracted with 999.7 g of 1,2-dichloroethane. The extract with the organic layer was concentrated under a reduced pressure to distill off 1,2-dichloroethane, was subjected to distillation under a reduced pressure and thereby yielded 160.1 g of methyl 1-acetyl-1-cyclopropanecarboxylate as a colorless liquid as a fraction at 75° C./20 mmHg.

[Spectral data]
$^1$H-NMR (CDCl$_3$) δ: 1.48 (s, 4H, cyclopropane), 2.48 (s, 3H, C$\underline{H}_3$COC), 3.75 (s, 3H, CH$_3$O)

Other embodiments and variations will be obvious to those skilled in the art, and this invention is not to be limited to the specific matters stated above.

What is claimed is:

1. A process for producing a 1-acyl-1-cyclopropanecarboxylate derivative, the process comprising the step of:

allowing a β-ketoester derivative represented by following Formula (1):

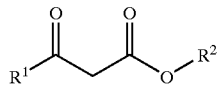

(1)

wherein $R^1$ is a hydrogen atom or a hydrocarbon group; and $R^2$ is a hydrocarbon group, to react with 1,2-dichloroethane to thereby yield a 1-acyl-1-cyclopropanecarboxylate derivative represented by following Formula (2):

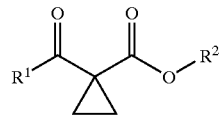

(2)

wherein $R^1$ and $R^2$ have the same meanings as defined above.

* * * * *